United States Patent
Rutten et al.

(10) Patent No.: US 8,160,722 B2
(45) Date of Patent: Apr. 17, 2012

(54) SUBCUTANEOUS LEAD FIXATION MECHANISMS

(75) Inventors: Jean J. G. Rutten, Bocholtz (NL); Leonardus J. C. Kretzers, Sittard (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 813 days.

(21) Appl. No.: 11/364,240

(22) Filed: Feb. 28, 2006

(65) Prior Publication Data
US 2007/0203556 A1    Aug. 30, 2007

(51) Int. Cl. *A61N 1/00* (2006.01)
(52) U.S. Cl. .......... 607/127; 607/128; 607/130
(58) Field of Classification Search .......... 607/127–128, 607/130
See application file for complete search history.

(56) References Cited

U.S. PATENT DOCUMENTS

| | | | | |
|---|---|---|---|---|
| 4,722,353 A * | 2/1988 | Sluetz | ............ | 607/128 |
| 4,957,118 A | 9/1990 | Erlebacher | | |
| 5,238,007 A | 8/1993 | Giele | | |
| 5,257,634 A * | 11/1993 | Kroll | ............ | 607/122 |
| 5,388,578 A | 2/1995 | Yomtov et al. | | |
| 5,476,498 A | 12/1995 | Ayers | | |
| 5,514,174 A * | 5/1996 | Heil et al. | ............ | 607/128 |
| 5,531,764 A | 7/1996 | Adams | | |
| 5,531,781 A | 7/1996 | Alferness | | |
| 5,871,532 A | 2/1999 | Schroeppel | | |
| 5,897,585 A | 4/1999 | Williams | | |
| 5,991,668 A | 11/1999 | Leinders | | |
| 6,096,064 A | 8/2000 | Routh | | |
| 6,136,005 A | 10/2000 | Goode et al. | | |
| 6,161,029 A | 12/2000 | Spreigl | | |
| 6,278,897 B1 * | 8/2001 | Rutten et al. | ............ | 607/122 |
| 2004/0059404 A1 | 3/2004 | Bjorklund et al. | | |

FOREIGN PATENT DOCUMENTS

| | | | |
|---|---|---|---|
| WO | WO2004091717 | * | 10/2004 |
| WO | WO2005122727 | | 12/2005 |

* cited by examiner

*Primary Examiner* — Nicole F Lavert
(74) *Attorney, Agent, or Firm* — Michael C. Soldner

(57) ABSTRACT

A medical device that includes a lead having a lead body extending from a proximal end to a distal end, and a housing having a connector block for receiving the proximal end of the lead body. A fixation mechanism is positioned proximal to an electrode coil located at the distal end of the lead body, and a fixation member or a plurality of fixation members extend from the fixation mechanism from a fixation member proximal end to a fixation member distal end. The fixation members are advanceable from a first position corresponding to the fixation member distal end being positioned along the lead during subcutaneous placement of the lead, to a second position corresponding to the fixation member distal end being positioned away from the lead to fixedly engage the lead at a target site.

23 Claims, 5 Drawing Sheets

SUBCUTANEOUS LEAD FIXATION MECHANISMS

FIELD OF THE INVENTION

The present invention generally relates to an implantable subcutaneous lead for use with an implantable medical device, and more particularly, to a lead that includes deployable fixation means for positively fixating the lead at an implantation site.

BACKGROUND OF THE INVENTION

Many types of implantable medical devices (IMDs) have been clinically implanted over the last twenty years that deliver relatively high-energy cardioversion and/or defibrillation shocks to a patient's heart when a malignant tachyarrhythmia, e.g., atrial or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the EGM.

Current implantable cardioverter/defibrillators (ICDs) or implantable pacemaker/cardioverter/defibrillators (PCDs) include programmable parameters such as multiple arrhythmia detection criteria/levels, multiple therapy prescriptions (e.g., stimulation at pacing levels (atrial/ventricular/dual chamber atrial & ventricular for bradycardia, bi-atrial and/or bi-ventricular for heart failure patients and arrhythmia overdrive or entrainment stimulation) and high level stimulation via cardioversion and/or defibrillation), extensive diagnostic capabilities and high speed telemetry systems. These ICDs or PCDs are typically implanted into patients who have experienced a significant cardiac event.

Attempts at identifying those patients who are asymptomatic by conventional measures but are nevertheless at risk of a future sudden death episode are being undertaken. Current studies of patient populations, e.g., the MADIT II and SCD-HeFT studies, are establishing that there are large numbers of patients in any given population that are susceptible to sudden cardiac death, and that they can be identified with some degree of certainty. One option proposed for this patient population is to implant a prophylactic subcutaneous implantable cardioverter/defibrillator (SubQ ICD) to deliver therapy in the event of a cardiac episode, such as sudden cardiac arrest, in order to reduce the risk of death resulting from the episode, and who will then have a full-featured ICD with transvenous leads implanted.

Current implanted subcutaneous coil leads are complicated and time consuming to implant and may dislodge or pull back acutely. Further, fibrosis and tissue build-up make it impossible to remove intracardial leads after a few month of implant.

Therefore, for these and other reasons, a need exists for an improved method and apparatus for a subcutaneously implanted lead that is easy to implant and stays fixed in the proper location acutely and chronically, or until it becomes desirable to remove the lead for repositioning or remove the lead permanently.

BRIEF DESCRIPTION OF THE DRAWINGS

Embodiments of the present invention will be appreciated as the same becomes better understood by reference to the following detailed description of the specific embodiments of the invention when considered in connection with the accompanying drawings, in which like numbered reference numbers designate like parts throughout the figures thereof, and wherein.

DETAILED DESCRIPTION OF THE INVENTION

Figure 1:
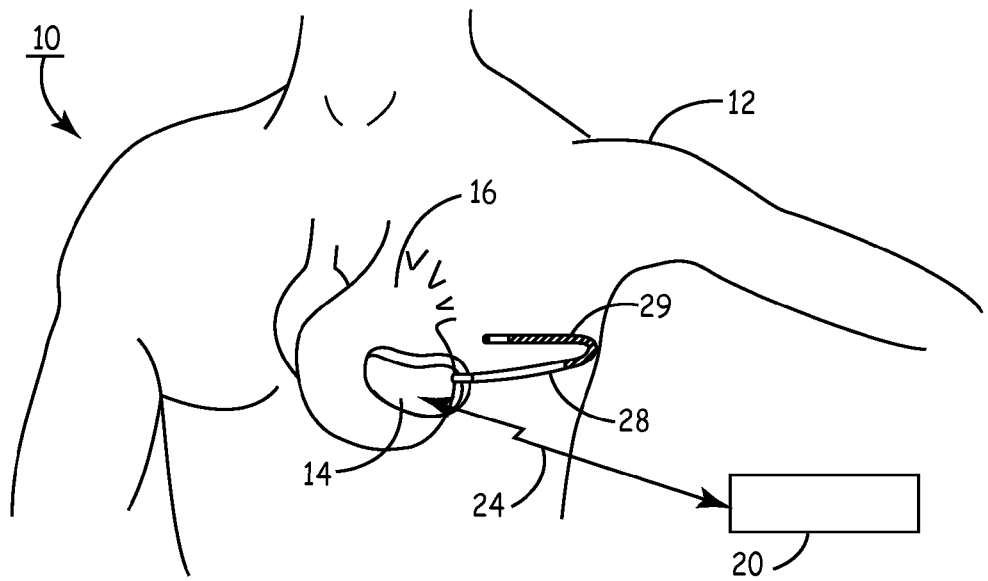
FIG. 1 is a schematic diagram of a subcutaneous medical device implanted in a patient according to an embodiment of the present invention.

FIG. 1 is a schematic diagram of a subcutaneous medical device implanted in a patient according to an embodiment of the present invention. As illustrated in FIG. 1, a subcutaneous medical device includes a hermetically sealed housing 14 that is subcutaneously implanted outside a patient's 12 ribcage anterior to the cardiac notch and a subcutaneous sensing and cardioversion/defibrillation therapy delivery lead 28 extending from the housing 14 to be positioned in relation to the heart 16. The cardiac notch is the lateral deflection of the anterior border/boundary of the left lung, which accommodates the space taken up by the heart. Lead 28 is tunneled subcutaneously from the median implant pocket of housing 14 laterally and posteriorly to the patient's back to a location opposite the heart such that the heart 16 is disposed between the housing 14 and a distal electrode coil 29 of subcutaneous lead 28.

Further referring to FIG. 1, a programmer 20 may be positioned in telemetric communication with circuitry contained within housing 14 via an RF communication link 24, such as Bluetooth, WiFi, MICS, for example, or as described in U.S. Pat. No. 5,683,432 "Adaptive Performance-Optimizing Communication System for Communicating with an Implantable Medical Device" to Goedeke, et al and incorporated herein by reference in its entirety.

Figure 2A:
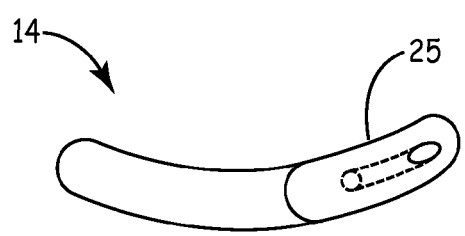
FIG. 2A is a top view of a device housing according to an embodiment of the present invention.
Figure 2B:
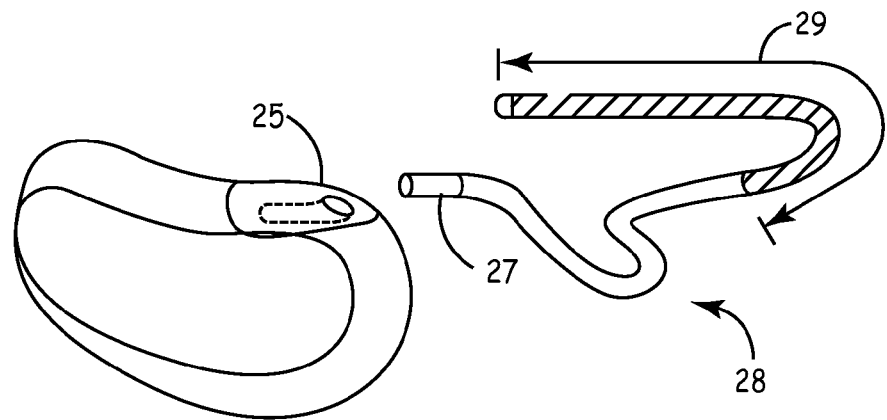
FIG. 2B is a schematic diagram of a device housing and a lead according to an embodiment of the present invention.

FIG. 2A is a top view of a device housing according to an embodiment of the present invention. FIG. 2B is a schematic diagram of a device housing and a lead according to an embodiment of the present invention. As illustrated in FIGS. 2A and 2B, housing 14 may have a concave, substantially kidney shaped, for example, with a connector block 25 for receiving a proximal connector pin 27 of subcutaneous sensing and cardioversion/defibrillation therapy delivery lead 28 and electrically connecting the lead 28 to the circuitry within housing 14. Housing 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronic circuitry located in housing 14 of subcutaneous cardioverter-defibrillator (described later in relation to FIGS. 3-4) may be incorporated on a polyamide flex circuit, printed circuit board (PCB) or ceramic substrate with integrated circuits packaged in leadless chip carriers and/or chip scale packaging (CSP). Housing 14 is formed having a concave construction enabling un-obtrusive subcutaneous implant by the concave structure of the canister following the natural curve of the patient's median ribcage at the cardiac notch. This structure also minimizes patient discomfort when seated, bending over and/or during normal torso movement.

The electronic circuitry in housing 14 (as described above in relation to FIGS. 1-2) includes circuitry for performing any desired known sensing and or/therapy delivery function(s), such as detection a tachyarrhythmia from the sensed ECG and delivering cardioversion/defibrillation therapy, as well as post-shock pacing as needed while the heart recovers. A simplified block diagram of such circuitry adapted to function employing the first and second and, optionally, the third cardioversion-defibrillation electrodes as well as the ECG sensing and pacing electrodes described above is set forth in FIG. 3. It will be understood that the simplified block diagram does not show all of the conventional components and circuitry of such ICDs including digital clocks and clock lines, low voltage power supply and supply lines for powering the circuits and providing pacing pulses or telemetry circuits for telemetry transmissions between housing of the SubQ ICD and an external programmer (20 of FIG. 1).

Figure 3:
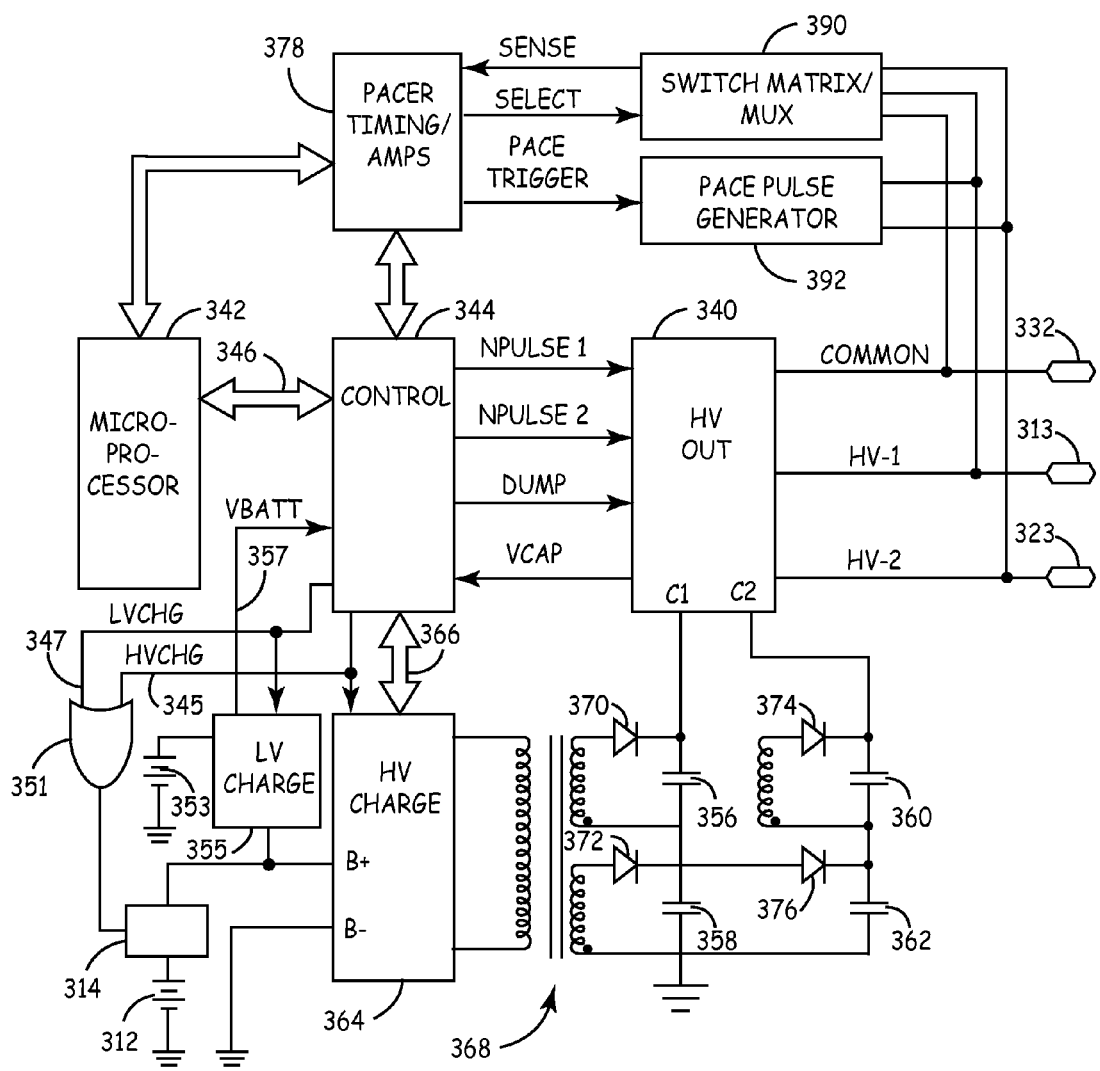
FIG. 3 is a schematic diagram of electronic circuitry included in a medical device according to an embodiment of the present invention.

FIG. 3 is a schematic diagram of electronic circuitry included in a medical device according to an embodiment of the present invention. As illustrated in FIG. 3, a low voltage battery 353 is coupled to a power supply (not shown) that supplies power to the ICD circuitry and the pacing output capacitors to supply pacing energy in a manner well known in the art. The low voltage battery may include one or two conventional $LiCF_x$, $LiMnO_2$ or $LiI_2$ cells, for example, and a high voltage battery 312 may include one or two conventional LiSVO or $LiMnO_2$ cell.

In FIG. 3, ICD functions are controlled by means of stored software, firmware and hardware that cooperatively monitor the EGM, determine when a cardioversion-defibrillation shock or pacing is necessary, and deliver prescribed cardioversion-defibrillation and pacing therapies. The schematic diagram of FIG. 3 incorporates circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, for example, both incorporated herein by reference in their entireties, for selectively delivering single phase, simultaneous biphasic and sequential biphasic cardioversion-defibrillation shocks typically employing an ICD IPG housing electrode coupled to the COMMON output 312 of high voltage output circuit 340 and one or two cardioversion-defibrillation electrodes disposed posteriorly and subcutaneously and coupled to the HV-1 and HV-2 outputs (313 and 323, respectively) of the high voltage output circuit 340. The circuitry of the SubQ ICD 14 of the present invention can be made simpler by adoption of one such cardioversion-defibrillation shock waveform for delivery simply between the first and second cardioversion-defibrillation electrodes 313 and 323 coupled to the HV-1 and HV-2 outputs respectively. Alternatively, the third cardioversion-defibrillation electrode 332 can be coupled to the COMMON output as depicted in FIG. 3 and the first and second cardioversion-defibrillation electrodes 313 and 323 can be electrically connected in to the HV-1 and the HV-2 outputs, respectively, as depicted in FIG. 3.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The SubQ ICD of the present invention uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation shocks are only delivered when a malignant tachyarrhythmia, e.g., ventricular fibrillation is detected through processing of the far field cardiac ECG employing one of the available detection algorithms known in the ICD art.

In FIG. 3, pacer timing/sense amplifier circuit 378 processes the far field ECG SENSE signal that is developed across a particular ECG sense vector defined by a selected pair of the electrodes 332, 313 and, optionally, electrode 323 if present as noted above. The selection of the sensing electrode pair is made through the switch matrix/MUX 390 in a manner to provide the most reliable sensing of the EGM signal of interest, which would be the R wave for patients who are believed to be at risk of ventricular fibrillation leading to sudden death. The far field ECG signals are passed through the switch matrix/MUX 390 to the input of a sense amplifier in the pacer timing/sense amplifier circuit 378. Bradycardia is typically determined by an escape interval timer within the pacer timing circuit 378 or the timing and control circuit 344, and pacing pulses that develop a PACE TRIGGER signal applied to the pacing pulse generator 392 when the interval between successive R-waves exceeds the escape interval. Bradycardia pacing is often temporarily provided to maintain cardiac output after delivery of a cardioversion-defibrillation shock that may cause the heart to slowly beat as it recovers function.

Detection of a malignant tachyarrhythmia is determined in the timing and control circuit 344 as a function of the intervals between R-wave sense event signals that are output from the pacer timing/sense amplifier circuit 378 to the timing and control circuit 344.

Certain steps in the performance of the detection algorithm criteria are cooperatively performed in a microcomputer 342, including microprocessor, RAM and ROM, associated circuitry, and stored detection criteria that may be programmed into RAM via a telemetry interface (not shown) conventional in the art. Data and commands are exchanged between microcomputer 342 and timing and control circuit 344, pacer timing/amplifier circuit 378, and high voltage output circuit 340 via a bidirectional data/control bus 346. The pacer timing/amplifier circuit 378 and the timing and control circuit 344 are clocked at a slow clock rate. The microcomputer 342 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 378. The algorithms and functions of the microcomputer 342 and timer and control circuit 344 employed and performed in detection of tachyarrhythmias are set forth, for example, in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al., U.S. Pat. No. 5,855,593 "Prioritized Rule Based Method and Apparatus for Diagnosis and Treatment of Arrhythmias" to Olson, et al. and U.S. Pat. No. 5,193,535 "Method and Apparatus for Discrimination of Ventricular Tachycardia from Ventricular Fibrillation and Treatment Thereof" to Bardy, et al., (all incorporated herein by reference in their entireties). Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '316, '186, '593 and '593 patents.

The detection algorithms are highly sensitive and specific for the presence or absence of life threatening ventricular arrhythmias, e.g., ventricular tachycardia (V-TACH) and ventricular fibrillation (V-FIB). Another optional aspect of the present invention is that the operational circuitry can detect the presence of atrial fibrillation (A FIB) as described in Olson, W. et al. "Onset And Stability For Ventricular Tachyarrhythmia Detection in an Implantable Cardioverter and Defibrillator," Computers in Cardiology (1986) pp. 167-170. Detection can be provided via R-R Cycle length instability detection algorithms. Once A-FIB has been detected, the operational circuitry will then provide QRS synchronized atrial cardioversion/defibrillation using the same shock energy and wave shapes used for ventricular cardioversion/defibrillation.

Operating modes and parameters of the detection algorithm are programmable and the algorithm is focused on the detection of V-FIB and high rate V-TACH (>240 bpm).

Although the ICD of the present invention may rarely be used for an actual sudden death event, the simplicity of design and implementation allows it to be employed in large populations of patients at modest risk with modest cost by medical personnel other than electrophysiologists. Consequently, the ICD of the present invention includes the automatic detection and therapy of the most malignant rhythm disorders. As part of the detection algorithm's applicability to children, the upper rate range is programmable upward for use in children, known to have rapid supraventricular tachycardias and more rapid V-FIB.

When a malignant tachycardia is detected, high voltage capacitors 356, 358, 360, and 362 are charged to a pre-programmed voltage level by a high-voltage charging circuit 364. It is generally considered inefficient to maintain a constant charge on the high voltage output capacitors 356, 358, 360, 362. Instead, charging is initiated when control circuit 344 issues a high voltage charge command HVCHG delivered on line 345 to high voltage charge circuit 364 and charging is controlled by means of bidirectional control/data bus 366 and a feedback signal VCAP from the HV output circuit 340. High voltage output capacitors 356, 358, 360 and 362 may be of film, aluminum electrolytic or wet tantalum construction.

The negative terminal of high voltage battery 312 is directly coupled to system ground. Switch circuit 314 is normally open so that the positive terminal of high voltage battery 312 is disconnected from the positive power input of the high voltage charge circuit 364. The high voltage charge command HVCHG is also conducted via conductor 349 to the control input of switch circuit 314, and switch circuit 314 closes in response to connect positive high voltage battery voltage EXT B+ to the positive power input of high voltage charge circuit 364. Switch circuit 314 may be, for example, a field effect transistor (FET) with its source-to-drain path interrupting the EXT B+ conductor 318 and its gate receiving the HVCHG signal on conductor 345. High voltage charge circuit 364 is thereby rendered ready to begin charging the high voltage output capacitors 356, 358, 360, and 362 with charging current from high voltage battery 312.

High voltage output capacitors 356, 358, 360, and 362 may be charged to very high voltages, e.g., 700-3150V, to be discharged through the body and heart between the selected electrode pairs among first, second, and, optionally, third subcutaneous cardioversion-defibrillation electrodes 313, 323, and 332. The details of the voltage charging circuitry are also not deemed to be critical with regard to practicing the present invention; one high voltage charging circuit believed to be suitable for the purposes of the present invention is disclosed. High voltage capacitors 356, 358, 360, and 362 are charged by high voltage charge circuit 364 and a high frequency, high-voltage transformer 368 as described in detail in commonly assigned U.S. Pat. No. 4,548,209 "Energy Converter for Implantable Cardioverter" to Wielders, et al. Proper charging polarities are maintained by diodes 370, 372, 374 and 376 interconnecting the output windings of high-voltage transformer 368 and the capacitors 356, 358, 360, and 362. As noted above, the state of capacitor charge is monitored by circuitry within the high voltage output circuit 340 that provides a VCAP, feedback signal indicative of the voltage to the timing and control circuit 344. Timing and control circuit 344 terminates the high voltage charge command HVCHG when the VCAP signal matches the programmed capacitor output voltage, i.e., the cardioversion-defibrillation peak shock voltage.

Timing and control circuit 344 then develops first and second control signals NPULSE 1 and NPULSE 2, respectively, that are applied to the high voltage output circuit 340 for triggering the delivery of cardioverting or defibrillating shocks. In particular, the NPULSE 1 signal triggers discharge of the first capacitor bank, comprising capacitors 356 and 358. The NPULSE 2 signal triggers discharge of the first capacitor bank and a second capacitor bank, comprising capacitors 360 and 362. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 344 serves to control operation of the high voltage output stage 340, which delivers high energy cardioversion-defibrillation shocks between a selected pair or pairs of the first, second, and, optionally, the third cardioversion-defibrillation electrodes 313, 323, and 332 coupled to the HV-1, HV-2 and optionally to the COMMON output as shown in FIG. 3.

Thus, ICD 10 monitors the patient's cardiac status and initiates the delivery of a cardioversion-defibrillation shock through a selected pair or pairs of the first, second and third cardioversion-defibrillation electrodes 313, 323 and 332 in response to detection of a tachyarrhythmia requiring cardioversion-defibrillation. The high HVCHG signal causes the high voltage battery 312 to be connected through the switch circuit 314 with the high voltage charge circuit 364 and the charging of output capacitors 356, 358, 360, and 362 to commence. Charging continues until the programmed charge voltage is reflected by the VCAP signal, at which point control and timing circuit 344 sets the HVCHG signal low terminating charging and opening switch circuit 314. Typically, the charging cycle takes only fifteen to twenty seconds, and occurs very infrequently. The ICD 10 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the ICD 10 on a prophylactic basis would be instructed to report each such episode to the attending physician for further evaluation of the patient's condition and assessment for the need for implantation of a more sophisticated and long-lived ICD.

Housing 14 may include telemetry circuit (not shown in FIG. 3), so that it is capable of being programmed by means of external programmer 20 via a 2-way telemetry link 24 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and C are Linke programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following commonly assigned U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device", each hereby incorporated by reference herein in their respective entireties.

Figure 4:
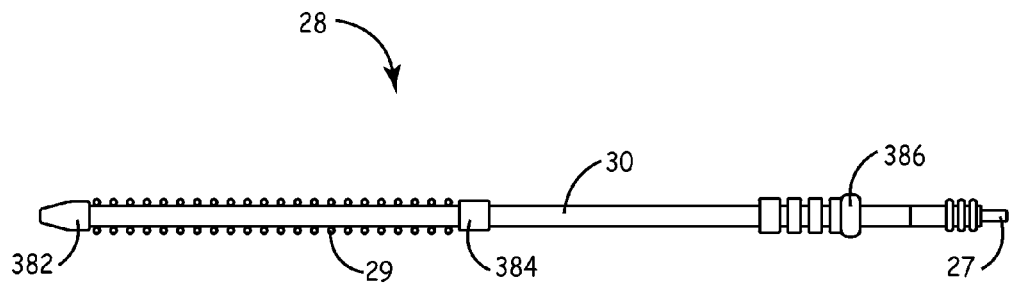
FIG. 4 is a schematic diagram of a subcutaneous lead of a medical device according to an embodiment of the present invention.

FIG. 4 is a schematic diagram of a subcutaneous lead of a medical device according to an embodiment of the present invention. As illustrated in FIG. 4, the lead 28 includes a lead body 30 that extends from lead connector pin 27 at the proximal end of the lead 28 to a distal tip 382 positioned at the distal end of the lead 28. A proximal suture sleeve 386 is positioned distally from the connector pin 27 and a distal electrode coil 29 is positioned at the distal end of the lead and extends proximally along the lead body 30 from the distal end of the lead 28. Lead 28 of the present invention includes a proximal fixation mechanism 384, and in such an embodiment the electrode coil 29 may extend from the distal tip 382 to the proximal fixation mechanism 384 so that the proximal fixation mechanism 384 is located just proximal to the electrode coil 29. The distal tip 382 may be formed of a flexible or pliant material such as polymeric material, silicone rubber or polyurethane. The electrode coil 29 may be formed of platinum, titanium or platinum iridium alloy. The lead body 28 may be formed of any flexible insulating material such as silicone rubber or polyurethane. The proximal lead pin 27 is electrically coupled to an insulated cable extending the length of the lead body 28 and electrically coupled to the electrode coil 29.

Figures 5A, 5B:
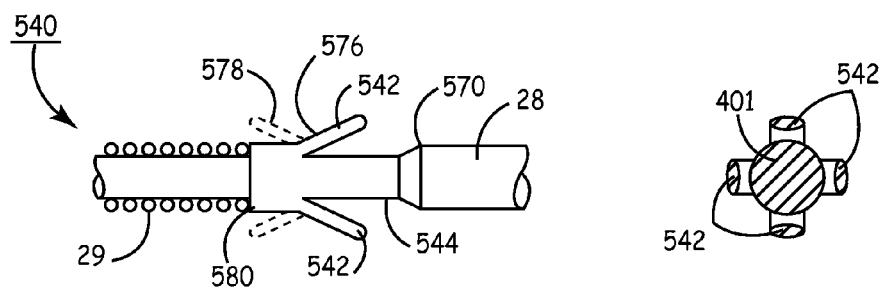
FIG. 5A is a side view of fixation apparatus positioned at a proximal end of a coil electrode of a subcutaneous lead of a medical device according to an embodiment of the present invention.
FIG. 5B is an end view of the distal end of the subcutaneous lead of FIG. 5A.

FIG. 5A is a side view of fixation apparatus positioned at a proximal end of a coil electrode of a subcutaneous lead of a medical device according to an embodiment of the present invention. FIG. 5B is an end view of the distal end of the subcutaneous lead of FIG. 5A. As illustrated in FIGS. 5A and 5B, the proximal fixation apparatus 540 is positioned proximal from the coil electrode 29 of the lead 28, and includes 4 proximal times 542 formed of flexible or pliant material such as polymeric materials for example, as silicone rubber or polyurethane. The fixation apparatus 540 extends from a proximal end 570 to a distal end 580, with the distal end 580 having a diameter greater than the proximal end 570 corresponding to the thickness of one of the times 542 so that the times 542 fold back and engage against a body portion 544 of the fixation apparatus 540 when the lead 28 is positioned within a tunneling sheath. Upon delivery to the proper location, the sheath is retracted from the lead 28 allowing the times 542 to return to their extended position 576 whereby they push against the subcutaneous tunneled wall improving both acute and chronic fixation. For chronic lead removal, the times 542 will reverse their orientation to be in a retraction position 578 extending in a direction opposite when in the extended position 576, toward the distal electrode coil 29, during lead retraction thus enabling ease of removal. This embodiment has an advantage in that the thickest portion of the lead is not located at the distal end of the lead near the spinal column but more on the patient's lateral side thus promoting less patient discomfort.

Figure 6A:
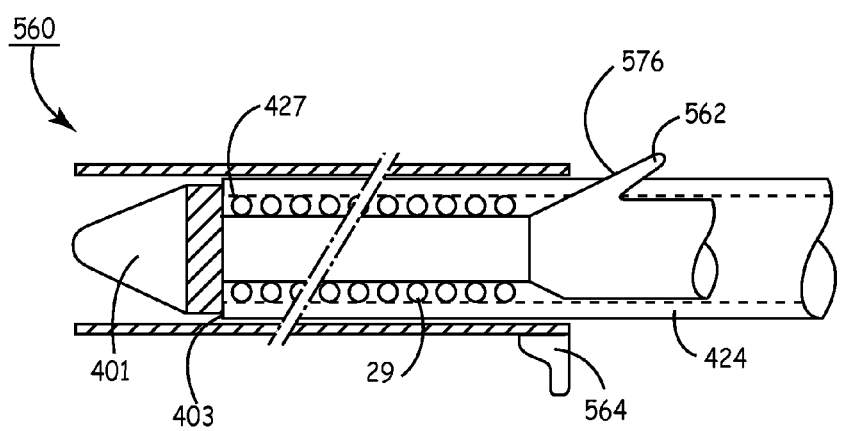
FIG. 6A is a side cut-away view of a subcutaneous lead of a medical device representing an embodiment of the present invention relating to a proximal fixation apparatus for anchoring subcutaneously tunneled lead.
Figure 6B:
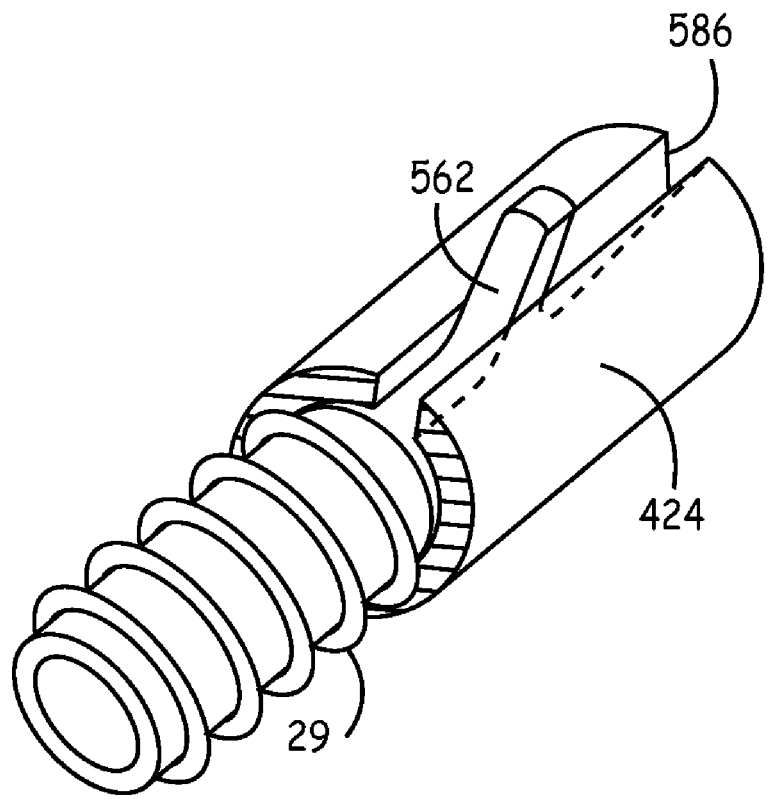
FIG. 6B is an oblique cut-away view of subcutaneous lead of FIG. 6A.
Figure 6C:
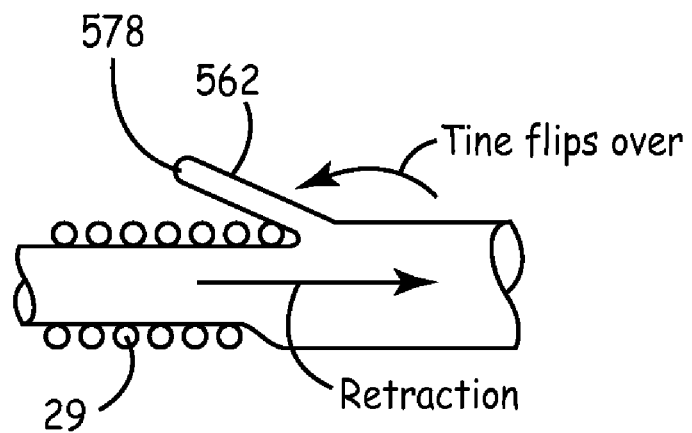
FIG. 6C is a side cut-away view of a subcutaneous lead of FIG. 6A showing further aspects of the invention.

FIG. 6A is a side cut-away view of a subcutaneous lead of a medical device representing an embodiment of the present invention relating to a proximal fixation apparatus for anchoring subcutaneously tunneled lead. FIG. 6B is an oblique cut-away view of subcutaneous lead of FIG. 6A. FIG. 6C is a side cut-away view of a subcutaneous lead of FIG. 6A showing further aspects of the invention. According to an embodiment of the present invention, a proximal fixation apparatus 560 includes a single proximal time 562 formed of flexible or pliant material, for example, polymeric materials such as silicone rubber or polyurethane. The time 562 is positioned within a longitudinal slot 564 formed along the length of a tunneling sheath 424 when the lead 28 is positioned the sheath 424.

The distal tip 401 of lead 28 includes a proximal end 403 that has a diameter greater than the diameter of the sheath 424 so that a distal end 427 of the sheath 424 engages against the proximal end 403 of the distal tip 401 as the sheath 424 is advanced through an introducer 564 (perspective view FIG. 6B). Upon delivery of the lead 28 to the proper location, the introducer 564 is removed from the sheath 424 by being slit using a slitting tool, for example, or other means known in the art. Because of the longitudinal slot 424 located along the sheath 424, the sheath does not have to be slit in order to remove the sheath 424 from the lead 28 subsequent to removing the introducer. Rather, the time 562 advances through the slot 564 as the sheath 424 is retracted. In addition to reducing the effort required to remove the sheath 424 from the lead 28, by enabling the time 562 to be positioned within the slot 564, the present invention reduces the length of the diameter required of the sheath 424 since the inner diameter of the sheath 424 does not have to accommodate the time 562, thereby reducing the required size of the introducer 564. Retraction of the sheath 424 allows the time 562 to push against the tunneled subcutaneous wall improving both acute and chronic fixation. For chronic lead removal, the time 562 will flip over during lead retraction from an extended position 576 away from coil electrode 29 to a retraction position 578 extending in a direction opposite to when the time 562 is in the extended position 576, toward the distal electrode coil 29, for ease of removal (FIG. 6C).

Figure 7:
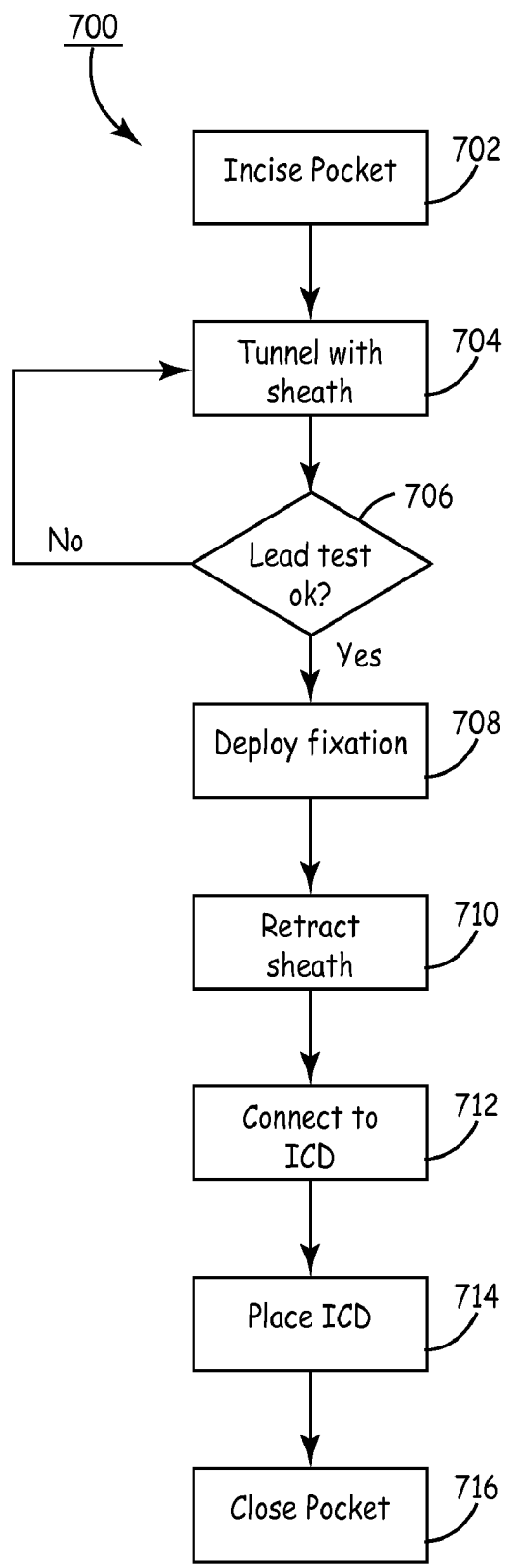
FIG. 7 is a flow chart of a method of fixedly positioning a subcutaneous lead according to an embodiment of the present invention.

FIG. 7 is a flow chart of a method of fixedly positioning a subcutaneous lead according to an embodiment of the present invention. As illustrated in FIG. 7 at step 702, the physician incises the subcutaneous implant site pocket for the housing 14 medially anterior to the cardiac notch. At step 704, the physician tunnels with an introducer/tunneling tool subcutaneously from the median implant pocket of housing 14 laterally and posterially to the patient's back to a location opposite the heart such that the heart 16 is disposed between the housing 14 and the distal end of subcutaneous lead 28. Tunneling is typically just above muscle subcutaneously crossing over ribs to prevent inadvertent entrance into the thoracic cavity/lungs. The implant location of device 14 and lead 28 is typically between the $3^{rd}$ and $8^{th}$ ribs. At step 706, the location of the electrode 29 of lead 28 is tested for proper sensing and positioning. If the test results are adequate, the process continues to step 708. If however, at step 706 the test results are inadequate, the process returns to step 704 to further continue tunneling and repositioning the electrode 29. At step 708, the physician deploys the fixation apparatus of the present invention. For example, with the lead designs as described above in relation to FIGS. 5 and 6, the sheath is retracted to deploy the inventive fixation apparatus.

Continuing with flow diagram 700, at step 710, the housing 14 is connected to the subcutaneous lead 28 proximal pin 27. At step 712 the SubQ ICD is placed in the implant pocket and the incision closed at step 714. Additional testing and programming via external programmer 20 may subsequently then be performed as is well know in the art.

It will be apparent from the foregoing that while particular embodiments of the invention have been illustrated and described, various modifications can be made without departing from the spirit and scope of the invention.

Accordingly, it is not intended that the invention be limited, except as by the appended claims.

What is claimed is:

1. A medical device system to be subcutaneously placed at a target site posterior to a heart of a patient, comprising:
   an electrode;
   a lead having a lead body extending from a proximal end to a distal end and defining a lead axis, the electrode being positioned along the lead;
   a fixation mechanism positioned along the lead body proximal to the electrode; and
   a plurality of fixation members extending from the fixation mechanism, each of the plurality of fixation members being pliant and forming a fixation member proximal end and a fixation member distal end, each of the plurality of fixation members having:
      a first position corresponding to the fixation member distal end being positioned generally against the lead body during subcutaneous placement of the electrode;
      a second position corresponding to the fixation member distal end being positioned away from the lead at an acute angle to the lead axis toward the proximal end of the lead to fixedly engage the electrode at the target site, each of said plurality of fixation members being resiliently biased toward the second position; and
      a third position corresponding to the fixation member distal end being positioned away from the lead at an acute angle to the lead axis toward the distal end of the lead.

2. The medical device system of claim 1, further comprising a plurality of channels formed along the lead to receive the plurality of fixation members in the first position.

3. The medical device system of claim 1, further comprising a sheath capable of being positioned over the plurality of fixation members to position each of said plurality of fixation members in the first position and being removable from the fixation mechanism to advance the plurality of fixation members to the second position.

4. The medical device system of claim 1, further comprising a sheath having a length and configured to receive the lead, wherein the sheath includes a cutout portion extending the length of the sheath for receiving the plurality of fixation members as the lead is advanced through the sheath.

5. The medical device system of claim 4, further comprising an introducer for receiving the sheath, wherein the sheath extends to a distal end and has a diameter less than a diameter of a proximal end of the electrode, the distal end of the sheath engaged against the proximal end of the electrode, when the lead is positioned within the sheath, to advance the lead within the introducer.

6. The medical device system of claim 4, wherein the fixation member distal end ends outward from the sheath via the cutout portion.

7. The medical device system of claim 1, further comprising a housing having a connector block for receiving the proximal end of the lead body.

8. A medical device system to be subcutaneously placed at a target site in a patient, comprising:
   a coil electrode;
   a lead having a lead body extending from a proximal end to a distal end and defining a lead axis, the coil electrode being positioned along the lead;
   a fixation mechanism positioned along the lead body proximal to the coil electrode, the fixation mechanism extending from a proximal end having a first diameter approximately equal to a diameter of the lead and a distal end having a second diameter greater than the first diameter; and
   a plurality of fixation members extending from the fixation mechanism being pliant and forming a fixation member proximal end and a fixation member distal end, each of the plurality of fixation members having:
      a first position corresponding to the fixation member distal end being positioned generally against the first diameter of the lead during subcutaneous placement of the electrode,
      a second position corresponding to the fixation member distal end being positioned away from the lead at an acute angle to the lead axis toward the proximal end of the lead to fixedly engage the coil electrode at the target site, each of said plurality of fixation members being resiliently biased toward the second position; and a third position corresponding to the fixation member distal end being positioned away from the lead at an acute angle to the lead axis toward the distal end of the lead.

9. The medical device system of claim 8, further comprising a sheath having a length and configured to receive the lead, wherein the sheath includes a cutout portion extending the length of the sheath for receiving the plurality of fixation members as the lead is advanced through the sheath.

10. The medical device system of claim 9, further comprising an introducer for receiving the sheath, wherein the sheath extends to a distal end and has a diameter less than a diameter of a proximal end of the electrode, the distal end of the sheath engaged against the proximal end of the electrode, when the lead is positioned within the sheath, to advance the lead within the introducer.

11. The medical device system of claim 10, wherein the fixation member distal end ends outward from the sheath via the cutout portion.

12. The medical device system of claim 11, wherein the electrode is positioned at a distal end of the lead and the plurality of fixation members extend away from the electrode when the plurality of fixation members are in the first and the second position and extend toward the electrode when the plurality of fixation members are in a third position during extraction of the lead.

13. The medical device system of claim 12, further comprising a housing having a connector block for receiving the proximal end of the lead body.

14. The medical device system of claim 9, further comprising a sheath capable of being positioned over the plurality of fixation members to position each of said plurality of fixation members in the first position and being removable from the fixation mechanism to advance the plurality of fixation members to the second position.

15. A method of subcutaneously positioning a lead of a medical device system to a target site distinct from a heart of a patient, the lead having a lead axis and an electrode located along a distal end of the lead and a fixation mechanism positioned along the lead body proximal to the electrode, the fixation mechanism having a plurality of fixation members each being pliant and having a fixation member proximal end and a fixation member distal end, comprising:

advancing a distal end of a first elongated member to the target site;

inserting the lead within the first elongated member, the inserting advancing the plurality of fixation members from a first position corresponding to the fixation member distal end being resiliently biased to be positioned away from the lead at an acute angle to the lead axis toward the proximal end of the lead, to a second position corresponding to the fixation member distal end being positioned generally against the lead during subcutaneous placement of the electrode; and extending the electrode and the fixation mechanism outward from the distal end of the first elongated member proximate the target sit to advance the plurality of fixation members from second position to the first position to fixedly engage the electrode at the target site; then retracting the lead from proximate the target site to advance the plurality of fixation members from the first position to a third position corresponding to the fixation member distal end being positioned away from the lead at an acute angle to the lead axis toward the distal end of the lead.

16. The method of claim 15, further comprising inserting the lead within a second elongated member having a length prior to the inserting the lead into the first elongated member, the second elongated member having a cutout portion extending the length of the second elongated member for receiving the plurality of fixation members as the lead is advanced through the second elongated member.

17. The method of claim 16, wherein the second elongated member extends to a distal end and has a diameter less than a diameter of a proximal end of the electrode, the distal end of the second elongated member engaged against the proximal end of the electrode, when the lead is positioned within the second elongated member, to advance the lead within the first elongated member.

18. The method of claim 17, wherein the plurality of fixation members extend away from the electrode when the plurality of fixation members are in the first and the second position and extend toward the electrode when the plurality of fixation members are in a third position.

19. A medical device system comprising:
a lead having a lead body extending from a proximal end to a distal end and defining a lead axis;
an electrode positioned along the lead body; and
a fixation mechanism positioned along the lead body including at least one fixation member extending from the fixation mechanism, being pliant and configured to maintain the lead in a fixed position relative to a body after subcutaneous placement, wherein the at least one fixation member is resiliently biased in a first position to extend in a first direction toward the proximal end of the lead at an acute angle relative to the lead axis, and change to a second position during lead retraction to extend in a second direction toward the distal end of the lead and at an acute angle relative to the lead axis.

20. The medical device system of claim 19, further comprising where the at least one fixation member is made of a flexible material.

21. The medical device system of claim 19, further comprising where the electrode is a coil electrode extending between the fixation mechanism and the distal end.

22. The medical device system of claim 19, further comprising a device coupled to the proximal end of the lead body.

23. The medical device system of claim 19, further comprising a sheath capable of being positioned over the plurality of fixation members to position each of said plurality of fixation members in a third position corresponding to the fixation member distal end being positioned generally against the lead during subcutaneous placement of the electrode and being removable from the fixation mechanism to advance the plurality of fixation members to the first position.

* * * * *